US005304163A

United States Patent [19]

Bonnici et al.

[11] Patent Number: 5,304,163

[45] Date of Patent: Apr. 19, 1994

[54] INTEGRAL RECONSTITUTION DEVICE

[75] Inventors: Paul J. Bonnici, Bolton; H. Edward Chase, Toronto; Douglas S. Sommerville, Newmarket, all of Canada

[73] Assignee: Baxter International Inc., Deerfield, Ill.

[21] Appl. No.: 471,573

[22] Filed: Jan. 29, 1990

[51] Int. Cl.$^{5}$ .......... A61M 5/00

[52] U.S. Cl. .......... 604/403; 4/414; 4/415

[58] Field of Search .......... 604/403, 404, 408–416; 128/DIG. 24

[56] References Cited

U.S. PATENT DOCUMENTS

| | | | |
|---|---|---|---|
| Re. 29,656 | 6/1978 | Chittenden et al. . | |
| 3,788,369 | 1/1974 | Killinger . | |
| 3,882,909 | 5/1975 | Ogle . | |
| 3,941,171 | 3/1976 | Ogle . | |
| 3,976,073 | 8/1976 | Quick et al. . | |
| 3,987,791 | 10/1976 | Chittenden et al. . | |
| 4,386,622 | 6/1983 | Munsch | 604/408 X |
| 4,396,383 | 8/1983 | Hart | 604/404 X |
| 4,410,321 | 10/1983 | Pearson et al. . | |
| 4,411,662 | 10/1983 | Pearson . | |
| 4,432,755 | 2/1984 | Pearson . | |
| 4,434,822 | 3/1984 | Bellamy et al. . | |
| 4,458,733 | 7/1984 | Lyons . | |
| 4,465,488 | 8/1984 | Richmond et al. . | |
| 4,484,920 | 11/1984 | Kaufman et al. . | |
| 4,507,114 | 3/1985 | Bohman et al. . | |
| 4,516,977 | 5/1985 | Herbert | 604/415 |
| 4,560,382 | 12/1985 | Isono . | |
| 4,564,054 | 1/1986 | Gustavsson . | |
| 4,583,971 | 4/1986 | Bocquet et al. . | |
| 4,589,879 | 5/1986 | Pearson . | |
| 4,607,671 | 8/1986 | Aalto et al. | 604/416 X |
| 4,624,667 | 11/1986 | Rutnarak . | |
| 4,675,020 | 6/1987 | McPhee . | |
| 4,759,756 | 7/1988 | Forman et al. . | |
| 4,787,429 | 11/1988 | Valentini et al. . | |
| 4,871,354 | 10/1989 | Conn et al. . | |
| 4,898,209 | 2/1990 | Zdeb . | |
| 4,969,883 | 11/1990 | Gilbert et al. . | |
| 5,002,530 | 3/1991 | Recker et al. . | |

FOREIGN PATENT DOCUMENTS

| | | |
|---|---|---|
| 0273015 | 6/1988 | European Pat. Off. . |
| 88124606 | 2/1989 | Fed. Rep. of Germany . |

*Primary Examiner*—Robert A. Hafer
*Assistant Examiner*—Sam Rimell
*Attorney, Agent, or Firm*—Paul E. Schaafsma; Amy L. H. Rockwell; Paul C. Flattery

[57] ABSTRACT

The device of the present invention includes a flexible container having an administration port and a flexible tube extending therefrom. The administration port includes an access membrane through which a spiked cannula can be inserted to gain access to the interior of the flexible container. The flexible tube contains a frangible or breakaway valve therein. Permanently secured to the end of the flexible tube is a sheath having a substantially circular base and an open-ended skirt including an inner surface depending from the base. The skirt includes a plurality of inwardly projecting bumps intermittently spaced around the inner surface to sealingly engage a standard drug vial. A sharp cannula is mounted within the skirt to pierce the stopper of the standard drug vial to establish fluid communication between the cannula and the interior of the drug vial. A peelable closure is provided covering the skirt opening prior to use to maintain a sterile condition of the device. A lumen is provided in housing to establish fluid communication between the cannula and the frangible or breakaway valve.

10 Claims, 3 Drawing Sheets

INTEGRAL RECONSTITUTION DEVICE

FIELD OF THE INVENTION

The present invention relates to the reconstitution of a drug by a diluent.

BACKGROUND OF THE INVENTION

Many drugs are mixed with a diluent before being delivered intravenously to a patient. The diluent may be, for example, a dextrose solution, a saline solution or even water. Many such drugs are supplied in powdered form and packaged in glass or plastic vials. Other drugs, such as some used in chemotherapy, are packaged in glass or plastic vials in a liquid state.

In order for the powdered drugs to be given intravenously to a patient, the drugs must first be placed in liquid form. Other drugs, although in a liquid state, must first be diluted before administration to the patient. As used herein, the term reconstitution includes not only liquidization of powdered drugs but also dilution of liquid drugs.

One way of reconstituting a drug is first to inject a drug diluent into the drug vial. This may be performed by a syringe having a liquid diluent contained in the syringe barrel. After the rubber stopper of the vial is pierced by the syringe needle, the liquid is injected into the vial. The vial is shaken to reconstitute and dilute the drug with the liquid. The liquid is then withdrawn back into the syringe. These steps may be repeated several times to ensure complete reconstitution of the drug. After the final mixing, the syringe is withdrawn and the reconstituted drug may then be injected into an administration set for intravenous administration to a patient.

Another common means of drug administration is to inject the reconstituted drug from the syringe into a parenteral solution container containing a medical solution such as dextrose or saline solution. The drug, now diluted with the medical solution in the parenteral solution container, is delivered through an administration set for intravenous administration to the patient.

Another means for reconstituting a drug is a device utilizing a double pointed needle. The double pointed needle includes a guide mounted around one end of the needle to direct the needle into fluid communication with the interior of a flexible solution container via a port. The opposite side of the needle includes a skirt which fits over and grips a drug vial to establish fluid communication between the needle and the interior of the drug vial.

An improvement to this is a device in which the guide and the skirt are attached to housing which establishes slidable engagement between the guide and the skirt. This allows fluid communication to be established between a lumen defined in the housing and the interior chamber of the flexible solution container while the drug vial can be attached to the skirt without establishing fluid communication between the interior of the vial and the lumen. When reconstitution is desired, the slidable housing is slid which directs one side of the needle into the vial to establish fluid communication for reconstitution.

Still another device utilizes a dedicated drug vial which is secured to a dedicated access site in a dedicated solution container. The dedicated access site includes housing to establish fluid communication between the interior of the dedicated drug vial and the interior of the dedicated flexible solution container.

As is seen, these devices all attempt to balance sterility issues which increase in difficulty as the complexity of the device increases with the issue of efficient storage of the drug prior to reconstitution. What would thus be advantageous is a reconstitution device which effectively reconstitutes and dilutes a drug. This device should also allow for easy storage of the unreconstituted drug preferably in a standard vial. This device should further avoid complexity of parts to reduce sterility difficulties. Such device should further be cost effective to produce and administer. The present invention meets these requirements.

SUMMARY OF THE INVENTION

The device of the present invention includes a flexible container having an administration port and a flexible tube extending therefrom. The administration port includes an access membrane through which a spiked cannula can be inserted to gain access to the interior of the flexible container. The flexible tube contains a frangible or breakaway valve therein. Permanently secured to the end of the flexible tube is a sheath having a substantially circular base and a skirt including an inner surface depending from the base. The skirt includes a plurality of inwardly projecting bumps intermittently spaced around the inner surface to sealingly engage a standard drug vial. A sharp cannula is mounted within the skirt to pierce the stopper of the standard drug vial to establish fluid communication between the cannula and the interior of the drug vial. A lumen is provided in housing to establish fluid communication between th cannula and the frangible or breakaway valve.

In storage, a peelable closure is provided over the skirt to ensure sterility. To use the device, the closure is peeled off and a standard drug vial is connected to the sheath with the sharp cannula piercing the stopper to establish fluid communication between the interior of the drug vial and the housing lumen. As a result of presterilization of the integral device and the sterile storage, an aseptic connection between the drug vial and the device is assured. When reconstitution is desired, the frangible or breakaway valve is opened thereby establishing fluid communication between the flexible tube and thus the interior of the flexible chamber and the lumen. Reconstitution can then proceed with the flexible container being squeezed to force liquid into the drug vial. With the flexible container inverted, air can be forced from the flexible container into the drug vial to remove the reconstituted drug. These stages can be repeated several times to ensure complete reconstitution of the drug.

BRIEF DESCRIPTIONS OF THE DRAWINGS

DETAILED DESCRIPTION OF A PREFERRED EMBODIMENT

Figure 1:
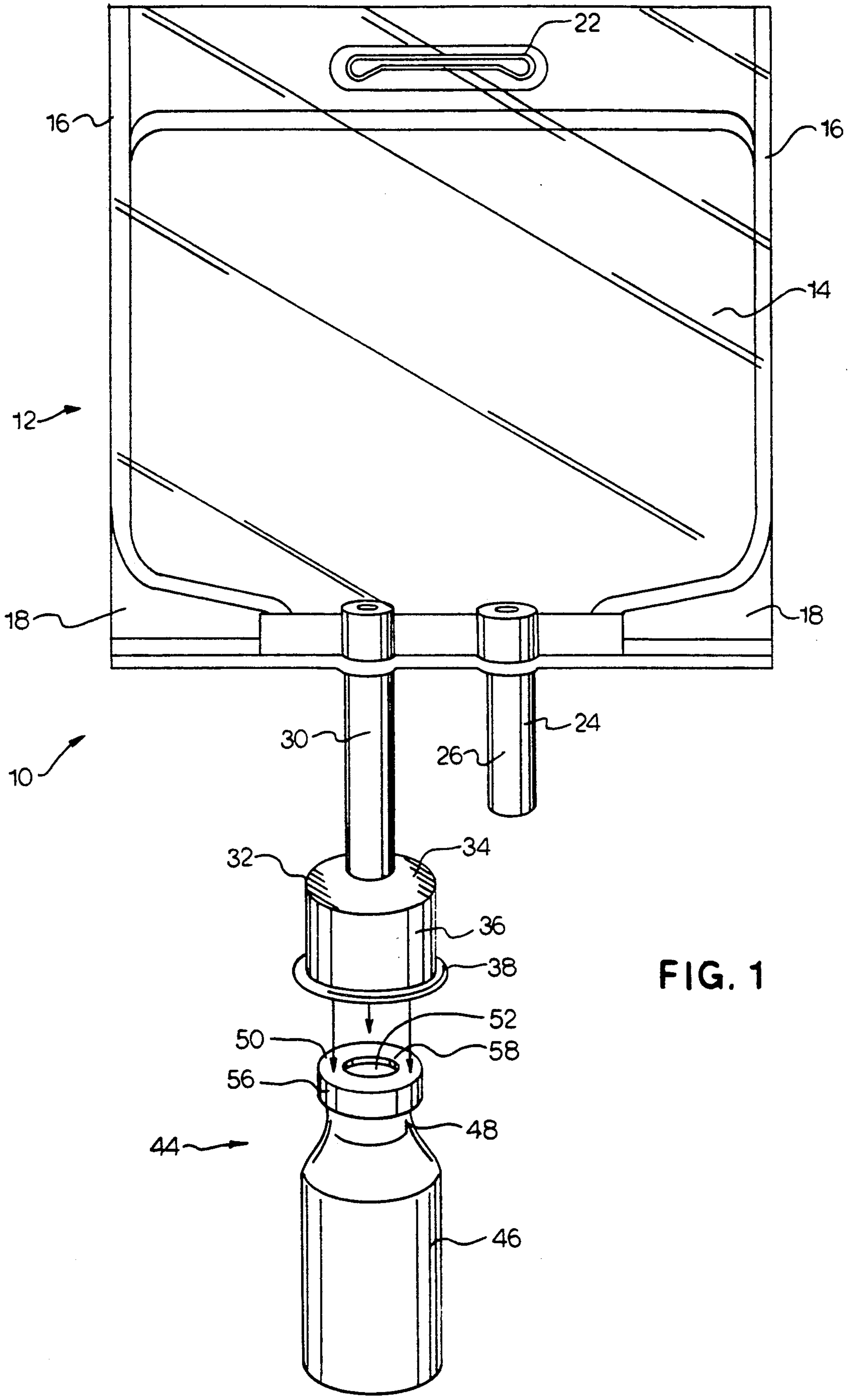
FIG. 1 is a perspective view of an embodiment of the invention made in accordance with the principles of the present invention.

Referring first to FIG. 1, a reconstitution device made in accordance with the principles of the present invention is designated generally by the reference numeral 10. The reconstitution device 10 includes a flexible walled medical parenteral solution container 12 as known in the art. The flexible container 12 includes two sheets of flexible plastic material 14 sealed together about their peripheries 16. Included in the sealed portion at the lower corners of the flexible container 12 are chevrons 18 shaped to help effect complete drainage. Additionally, at the top of the flexible container 12, an aperture 22 is formed in the seal on which the flexible container 12 can hang to administer the contents of the flexible container 12 intravenously.

The flexible container 12 includes at its lower periphery an administration port 24. The administration port 24 includes tubing 26 having in fluid communication with the interior of the flexible container 12 a membrane (not shown) of standard construction which closes off the administration port 24. A spike of a standard intravenous administration set (not shown) can be inserted into the tubing 26 which pierces the membrane to allow liquid in the container to exit the container, flow through an administration set, and into the intravenous system of a patient via a catheter.

Also extending from the lower periphery of the flexible container is flexible tubing 30 in fluid communication with the interior of the flexible container 17. Extending from the lower periphery of the flexible tubing 30 is an open ended sheath 32 which includes a base 34 and a skirt 36 projecting downwardly therefrom. A outwardly extending flange 38 is provided at the lower periphery of the skirt 36. Secured in a sealing engagement around the open end of the skirt 36 over the outwardly extending flange 38 is a peelable closure 40.

The present device 10 is adapted to be used in conjunction with a standard sized drug vial 44 which is also shown in FIG. 1. The drug vial 44 is typically made of an optically transparent glass or plastic, and includes a body 46, a neck 48 and a mouth 50. A resilient stopper 52 typically made of an elastomer is mounted within the mouth 50 to serve as an access site to the interior chamber of the drug vial 44.

The drug vial 44 typically further includes a malleable band 56 typically made of aluminum which is mounted about the outer periphery of the mouth 50 and the stopper 52, thereby retaining the stopper 52 within the drug vial 44. Typically, the malleable band 56 initially includes a top portion (not shown) covering the top of the stopper 52. This top portion is separated from the malleable band 56 by means of a weakened score line 58 disposed at the inner circle of the malleable band 56. This top portion is removed to provide access to the stopper 52.

Refer now to FIGS. 2 through 5. The skirt 36 defines an interior surface 62. Contained within the sheath 32 is a sharp, hollow cannula 64 which extends about the center axis of the skirt 36. The entire cannula 64 is contained within the sheath 32 with the sharp point 66 of the cannula 64 contained recessed from a plane defined by the open end of the skirt 32 and the outwardly extending flange 38. This recessed cannula 64 acts to reduce accidental "sticks" of personnel handling the device 10 as well as touch contamination of the device 10. Additionally provided about the open end of the sheath 32 is the peelable closure 40. The peelable closure 40 is preferably made of aluminum foil or other suitable barrier materials to bacteria and dirt. The peelable closure 40 is provided with a heat activated adhesive such that the peelable closure 40 is secured to the sheath 32 by heat sealing. The peelable closure 40 ensures sterility of the presterilized device 10 during storage and provides evidence of pre-use tampering.

Extending into the flexible tube 30 and molded integrally with the sheath member 32 is housing 68 defining a lumen 72. The lumen 72 is in fluid communication with the cannula 64. Thus, when the sheath 32 is placed over a drug vial 44 and the cannula 64 is inserted through the stopper 52 into the interior of the drug vial 44, open fluid communication is established between the interior of the drug vial 44 and the lumen 72.

Sealingly permanently engaged to the outer periphery of the lumen housing 68 and to the flexible tube 30 is a frangible or breakaway valve housing 74. The valve housing 74 is permanently secured to the interior of the flexible tubing 30 by solvent bonding or heat sealing. The valve housing 74 includes a tubular aperture 76 in fluid communication with the lumen 72. The lumen housing 68 is preferably tapered from an initial diameter to a smaller inner diameter. The valve housing 74 is preferably cooperatively tapered from an initial interior diameter to a smaller interior diameter. The taper of the outside diameter of the lumen housing 68 cooperates with the taper of the inside diameter of the valve housing 74 to form a tight fit. Additionally, the valve housing 74 and the lumen housing 68 are permanently sealed by means such as solvent bonding, heat bonding or other bonding techniques known in the art.

The tubular aperture 76 includes a normally closed end 80. The normally closed end 80 has extending from and integral with it an elongated, generally rigid handle 82. The normally closed end 80 further includes an annular zone of weakness 84 to facilitate breaking the handle 82 from the valve housing 74 thereby opening the valve. The valve housing 74 and the handle 82, which form the valve, are preferably a molded, chemically inert, rigid plastic. In a preferred embodiment, this plastic can be polyvinyl chloride.

The handle 82 includes a plurality of outwardly extending projections 86 which frictionally fit within the interior of the flexible tubing 30. The outwardly extending projections 86 dig into the interior of the tubing 30 and hold the handle in position after it is broken away from the closed end. This assures that fluid can flow in two directions, one way to provide medical liquid into the drug vial 44 and the opposite way to provide liquid from the drug vial 44 into the flexible container 12, without the handle 82 moving back into contact with the normally closed end 80 and blocking fluid flow.

Figure 3:
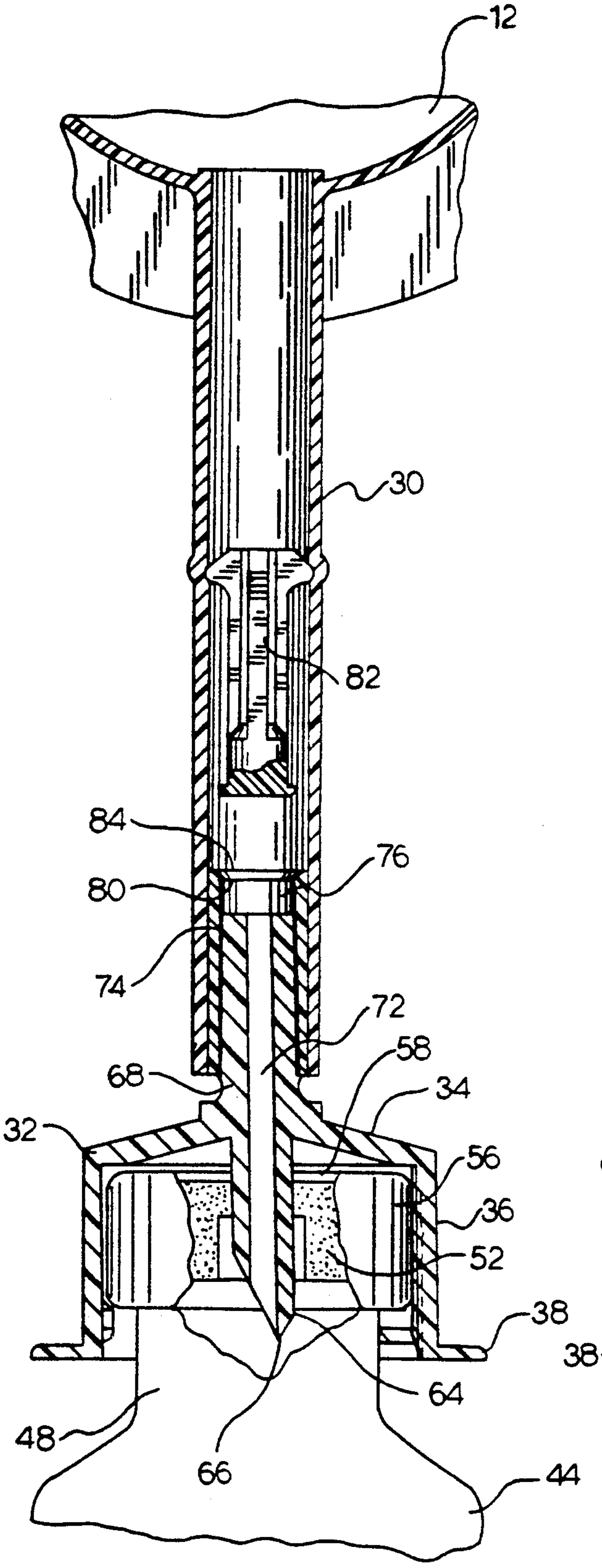
FIG. 3 is a cross sectional view of the device of FIG. 1 attached to a drug vial and with the frangible or breakaway valve open.
Figure 2:
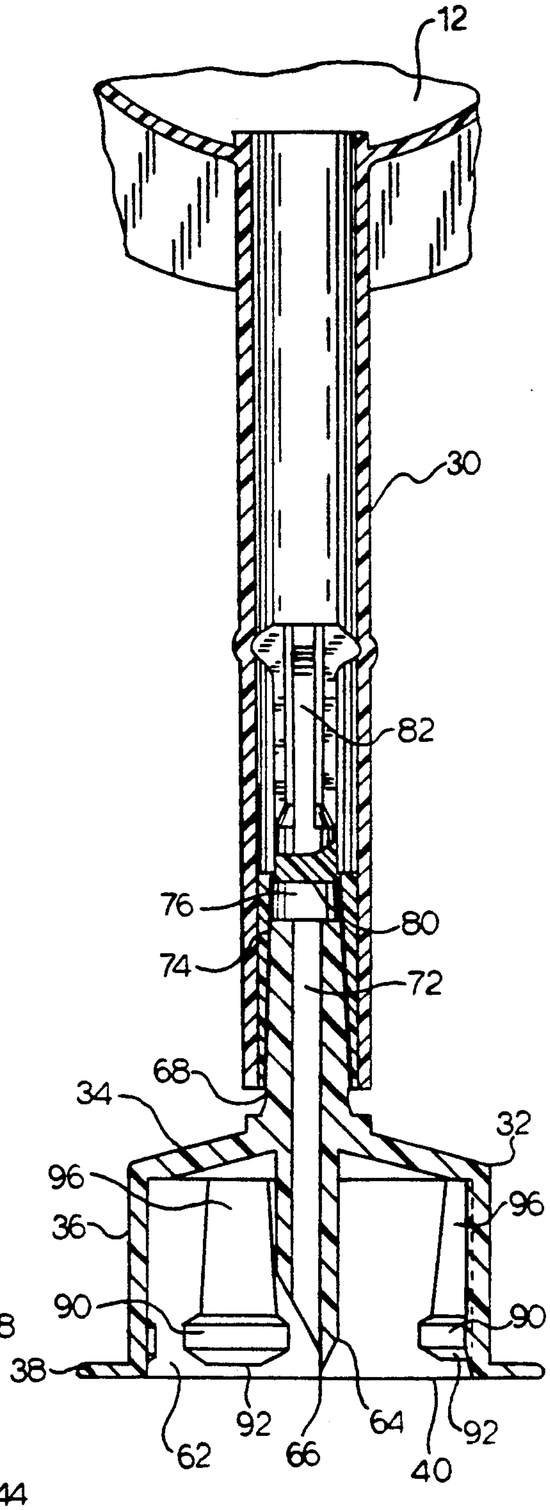
FIG. 2 is a cross sectional view of the device of FIG. 1.
Figure 4:
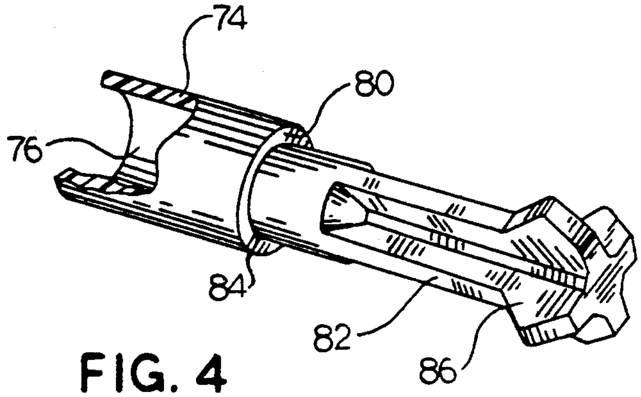
FIG. 4 is a perspective view, with portions broken away, of a frangible or breakaway valve in accordance with the principles of the present invention.
Figure 5:
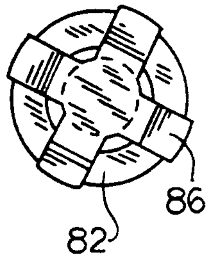
FIG. 5 is an end view of the frangible or breakaway valve of the present invention viewed from the elongated, generally rigid handle to the tubular portion.
Figure 6:
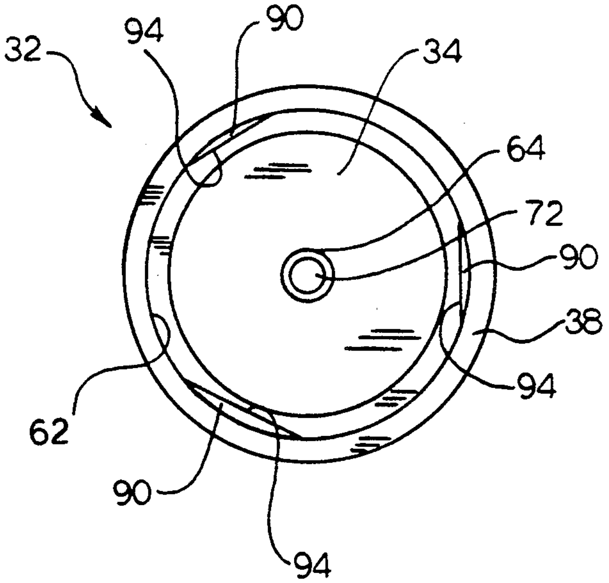
FIG. 6 is a bottom view of the sheath of the device of FIG. 1.

Referring now to FIG. 6 in conjunction with FIGS. 2 and 3, the sheath 32 includes a plurality of inwardly projecting bumps 90 intermittently spaced about the interior surface 62 of the skirt 36. The bumps 90 are all disposed a substantially equal distance from the base 34. This distance is substantially equal to the width of the malleable band 56 on the drug vial 44.

The bumps 90 are preferably spaced equal distance radially about the inner surface 62 of the skirt 36. Each bump 90 preferably includes a sloped side 92 facing the open end of the skirt 36. The slope side 92 extends to a plane 94 which represents the maximum internal projection of the bump 90. The plane of maximum projection 94 tapers on the base side to an elongated narrow plane 96 extending from the plane of maximum projection 94 to the base 34. The slope side 92 preferably defines an angle of about 30° from the inner surface 62 while the plane of maximum projection 94 is preferably at least about 0.026 inches from the inner surface 62.

The skirt 36 is preferably made of a semi-rigid material such as a polycarbonate or other suitable polymer. The semi-rigid skirt 36 assists in creating a tight fit between the device 10 and a wider size range of drug vials 44.

To use, the device 10 is installed on a drug vial 44 of standard construction by removing the foil closure 40 and simply pushing the sharp cannula 64 through the stopper 52. This penetration can be aided by use of a suitable lubricant on the cannula such as a silicon oil. The internal diameter of the skirt 36 is sized to approximate the outer diameter defined by the malleable band 56 used on most drug vials 44 of standard construction. Because the precise drug vial 44 dimensions vary throughout the industry, a tight fit is insured by the bumps 90, which create a stop against the underside of the malleable band 56, making inadvertent disconnection of the device and the drug vial 44 difficult.

The fit between the skirt 36 and the drug vial 44 is tight enough so that in most instances the bumps 90 deform the malleable band 56. This results in the creation of vertical grooves in the side of the malleable band 56 as the skirt 36 is pushed down about the mouth 48 of the drug vial 44. If the malleable band 56 is wider than average, there may be no space between the top of the malleable band 56 and the base 34 of the sheath 32. The width of the malleable band 56 may actually equal or even slightly exceed the distance between the base 34 and the base side of the bumps 90. In situations with wider malleable bands 56, the bumps 90 deform the underside of the malleable band 56 by causing indentation where the bumps 90 contact the underside.

After the sharp cannula 64 has been inserted into the drug vial 44 and fluid communication has been established between the interior of the drug vial 44 and the lumen 72, the device 10 can be stored for an extended period of time prior to use. This is because the permanently secured, integral design of the device 10 allows for presterilization of the entire unit, including the flexible container 12, the tubing 30, and the sheath 32. With the use of the peelable closure 40, the sterility of the device 10 during storage as well as the aseptic connection to drug vials 44 is assured. This assurance of sterility results in the availability of extended periods of storage prior to use.

When the drug is to be reconstituted, fluid communication can be established between the interior of the drug vial 44 and the interior of the flexible container 12 by opening the frangible or breakaway valve. To open the valve, the user can simply grasp the flexible tubing 30 to break the handle 82 from the valve housing 74 at the weakened score line 84. The valve housing 74 remains in place within the flexible tubing 30 since it is bonded to the interior of the flexible tubing 30. The outwardly extending projections 86 of the handle 82 maintain frictional contact with the interior of the flexible tubing 30 as the valve is opened and the handle 82 is "walked" down the flexible tubing 30 by manually bending and releasing the flexible tubing 30. A force created by folding the flexible tubing 30 back upon itself "walks" the handle 82 down the flexible tubing 30 where it remains after the force is released. The handle 82 can be "walked" further down the flexible tubing 30 by again folding the flexible tubing 30 back upon itself and releasing. The outwardly extending projections 86 assure that the handle 82 remains away from the aperture 76 by frictionally "biting" into the flexible tubing 30.

It should be understood that changes and modifications to the preferred embodiment described here and will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A device for reconstituting a drug contained in a drug vial having a mouth with a stopper contained therein, the device comprising:
   - a flexible container defining an interior and having at least two ports in fluid communication with the interior thereof;
   - one of the ports including a breakaway valve contained therein, the breakaway valve including valve housing permanently secured to the port;
   - a sheath permanently connected to the valve housing, the sheath being adapted to be secured to the drug vial, the sheath further including a hollow cannula disposed therein, the hollow cannula being adapted to pierce the drug vial stopper when the sheath is secured thereto; and
   - the hollow cannula being in fluid communication with the breakaway valve such that when the breakaway valve is closed, fluid communication between the hollow cannula and the interior of the flexible container is prevented while when the breakaway valve is open, fluid communication between the hollow cannula and the interior of the flexible container is allowed.

2. The device of claim 1 wherein the sheath includes a substantially circular base, a skirt depending from the base and defining an open end and an inner surface, and a plurality of inwardly projecting bumps on the inner surface of the skirt.

3. The device of claim 2 wherein the plurality of bumps are all disposed a substantially equal distance from the base, the distance being substantially equal to the width of a malleable band of a vial.

4. The device of claim 2 wherein the plurality of bumps includes a sloped side facing the open end of the skirt.

5. The device of claim 1 wherein the cannula defines a sharp outer periphery.

6. The device of claim 1 wherein the cannula defines an outer periphery which extends outwardly from the port a distance less than the sheath.

7. The device of claim 1 further including a peelable closure over the sheath.

8. The device of claim 1 wherein the breakaway valve includes a tubular portion having a closed end, a handle extending from and integral with the closed end of the tubular portion, and a zone of weakness positioned such that at least a portion of the closed end is removable by manipulating the handle to separate the closed end from the tubular portion to permit fluid flow through the breakaway valve.

9. The device of claim 8 wherein the handle includes projection means extending radially outwardly and being in frictional contact with the interior surface of the port such that after separation of the handle from the tubular portion the handle can be moved away from and remain away from the tubular portion.

10. The device of claim 8 wherein the zone of weakness is at the junction of the handle and the closed end.

* * * * *